(12) United States Patent
Zucherman et al.

(10) Patent No.: US 7,029,473 B2
(45) Date of Patent: Apr. 18, 2006

(54) DEFLECTABLE SPACER FOR USE AS AN INTERSPINOUS PROCESS IMPLANT AND METHOD

(75) Inventors: James F. Zucherman, San Franciscos, CA (US); Ken Y. Hsu, San Francisco, CA (US); Charles J. Winslow, Walnut Creek, CA (US); John J. Flynn, Concord, CA (US)

(73) Assignee: St. Francis Medical Technologies, Inc., Alameda, CA (US)

( * ) Notice: Subject to any disclaimer, the term of this patent is extended or adjusted under 35 U.S.C. 154(b) by 267 days.

(21) Appl. No.: 10/230,505

(22) Filed: Aug. 29, 2002

(65) Prior Publication Data

US 2003/0065330 A1 Apr. 3, 2003

Related U.S. Application Data (63) Continuation-in-part of application No. 10/037,236, filed on Nov. 9, 2001, which is a continuation-in-part of application No. 09/799,215, filed on Mar. 5, 2001, which is a continuation-in-part of application No. 09/179,570, filed on Oct. 27, 1998, now Pat. No. 6,048,342, which is a continuation-in-part of application No. 09/175,645, filed on Oct. 20, 1998, now Pat. No. 6,068,630.

(51) Int. Cl.
*A61B 17/70* (2006.01)

(52) U.S. Cl. ...................................... 606/61; 623/17.11
(58) Field of Classification Search ................... 606/60, 606/61, 72, 76; 623/17.11, 17.16
See application file for complete search history.

(56) References Cited

U.S. PATENT DOCUMENTS

| | | | |
|---|---|---|---|
| 2,456,806 A | 12/1948 | Wolffe | 33/174 |
| 2,677,369 A | 5/1954 | Knowles | |
| 3,426,364 A | 2/1969 | Lumb | |
| 3,648,691 A | 3/1972 | Lumb et al. | |
| 3,867,728 A | 2/1975 | Stubstad et al. | |
| 3,875,595 A | 4/1975 | Froning | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,479,491 A | 10/1984 | Martin | |
| 4,501,269 A | 2/1985 | Bagby | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,604,995 A | 8/1986 | Stephens et al. | |
| 4,611,582 A | 9/1986 | Duff | |
| 4,636,217 A | 1/1987 | Ogilvie et al. | |
| 4,643,178 A | 2/1987 | Nastari et al. | |
| 4,657,550 A | 4/1987 | Daher | |
| 4,685,447 A | 8/1987 | Iversen et al. | |
| 4,696,290 A | 9/1987 | Steffee | |
| 4,714,469 A | 12/1987 | Kenna | |
| 4,743,256 A | 5/1988 | Brantigan | |
| 4,772,287 A | 9/1988 | Ray et al. | |

(Continued)

OTHER PUBLICATIONS

Minns, R.J., et al., *Preliminary Design and Experimental Studies of a Novel Soft Implant for Correcting Sagittal Plane Instability in the Lumber Spine*, SPINE vol. 22, No. 16, pp. 1819–1825, © 1997, Lippincott–Raven Publishers.

(Continued)

*Primary Examiner*—David O. Reip
(74) *Attorney, Agent, or Firm*—Fliesler Meyer LLP (57) ABSTRACT

The present invention is a interspinous process device with a deflectable spacer which can be placed between adjacent spinous processes to limit the movement of the vertebrae. The device limits the range of motion of the spinous processes.

49 Claims, 6 Drawing Sheets

U.S. PATENT DOCUMENTS

| | | |
|---|---|---|
| 4,834,757 A | 5/1989 | Brantigan |
| 4,878,915 A | 11/1989 | Brantigan |
| 4,904,260 A | 2/1990 | Ray et al. |
| 4,904,261 A | 2/1990 | Dove et al. |
| 4,913,134 A | 4/1990 | Luque |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 5,011,484 A | 4/1991 | Breard |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,084,049 A | 1/1992 | Asher et al. |
| 5,092,866 A | 3/1992 | Breard et al. |
| 5,122,130 A | 6/1992 | Keller .................. 606/61 |
| 5,123,926 A | 6/1992 | Pisharodi |
| 5,167,662 A | 12/1992 | Hayes et al. |
| 5,180,381 A | 1/1993 | Aust et al. |
| 5,192,327 A | 3/1993 | Brantigan |
| 5,258,031 A | 11/1993 | Salib et al. |
| 5,263,953 A | 11/1993 | Bagby |
| 5,290,312 A | 3/1994 | Kojimoto et al. |
| 5,304,178 A | 4/1994 | Stahurski |
| 5,306,309 A | 4/1994 | Wagner et al. |
| 5,352,225 A | 10/1994 | Yuan et al. |
| 5,387,213 A | 2/1995 | Breard et al. |
| 5,390,683 A | 2/1995 | Pisharodi |
| 5,395,372 A | 3/1995 | Holt et al. |
| 5,415,661 A | 5/1995 | Holmes |
| 5,443,514 A | 8/1995 | Steffee |
| 5,454,812 A | 10/1995 | Lin |
| 5,458,638 A | 10/1995 | Kuslich et al. |
| 5,458,641 A | 10/1995 | Ramirez Jimenez |
| 5,458,643 A | 10/1995 | Oka et al. |
| 5,470,333 A | 11/1995 | Ray |
| 5,496,318 A | 3/1996 | Howland et al. |
| 5,505,732 A | 4/1996 | Michelson |
| 5,514,180 A | 5/1996 | Heggeness et al. |
| 5,527,312 A | 6/1996 | Ray |
| 5,534,028 A | 7/1996 | Bao et al. |
| 5,534,029 A | 7/1996 | Shima |
| 5,540,689 A | 7/1996 | Sanders et al. |
| 5,549,679 A | 8/1996 | Kuslich |
| 5,554,191 A | 9/1996 | Lahille et al. |
| 5,562,736 A | 10/1996 | Ray et al. |
| 5,593,409 A | 1/1997 | Michelson |
| 5,609,634 A | 3/1997 | Voydeville |
| 5,645,597 A | 7/1997 | Krapiva |
| 5,645,599 A | 7/1997 | Samani |
| 5,653,761 A | 8/1997 | Pisharodi |
| 5,658,286 A | 8/1997 | Sava |
| 5,674,295 A | 10/1997 | Ray et al. |
| 5,674,296 A | 10/1997 | Bryan et al. |
| 5,676,702 A | 10/1997 | Ratron |
| 5,702,455 A | 12/1997 | Saggar |
| 5,725,582 A | 3/1998 | Bevan et al. |
| 5,766,252 A | 6/1998 | Henry et al. |
| 5,800,438 A | 9/1998 | Tuke et al. .................. 606/90 |
| 5,824,098 A | 10/1998 | Stein |
| 5,865,846 A | 2/1999 | Bryan et al. |
| 5,885,299 A | 3/1999 | Winslow et al. |
| 5,888,224 A | 3/1999 | Beckers et al. |
| 5,888,226 A | 3/1999 | Rogozinski |
| 5,976,186 A | 11/1999 | Bao et al. |
| 6,001,130 A | 12/1999 | Bryan et al. |
| 6,022,376 A | 2/2000 | Assell et al. |
| 6,048,342 A | 4/2000 | Zucherman et al. |
| 6,068,630 A | 5/2000 | Zucherman et al. |
| 6,113,639 A | 9/2000 | Ray et al. |
| 6,156,067 A | 12/2000 | Bryan et al. |
| 6,190,414 B1 | 2/2001 | Young et al. |
| 6,234,705 B1 | 5/2001 | Troxel |
| 6,261,296 B1 | 7/2001 | Aebi et al. .................. 606/90 |
| 6,368,351 B1 | 4/2002 | Glenn et al. |
| 6,458,131 B1 | 10/2002 | Ray |
| 6,565,570 B1 | 5/2003 | Sterett et al. .................. 606/69 |
| 6,770,095 B1 | 8/2004 | Grinberg et al. |
| 2001/0012938 A1 | 8/2001 | Zucherman |
| 2004/0106998 A1 | 6/2004 | Ferree |
| 2004/0138750 A1 | 7/2004 | Mitchell |

FOREIGN PATENT DOCUMENTS

| | | |
|---|---|---|
| CA | 2015507 | 1/1991 |
| DE | 2821678 A1 | 4/1980 |
| DE | 3113142 A1 | 1/1982 |
| EP | 140790 A2 | 10/1984 |
| EP | 146347 A1 | 12/1984 |
| EP | 322334 A1 | 12/1988 |
| EP | 0677277 A2 | 10/1995 |
| EP | 0767636 B1 | 4/1997 |
| EP | 1138268 A1 | 10/2001 |
| FR | WO 90/00037 | 1/1990 |
| FR | 2681525 A1 | 3/1993 |
| FR | 2707864 A1 | 1/1995 |
| FR | 2717675 | 9/1995 |
| FR | 2722980 A1 | 2/1996 |
| FR | 2780269 A1 | 12/1999 |
| FR | 2782911 A1 | 3/2000 |
| FR | 2806614 A1 | 9/2001 |
| FR | 2806616 A1 | 9/2001 |
| SU | 1484348 A1 | 6/1989 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |

OTHER PUBLICATIONS

Waldemar Link, brochure entitled *Wirbelsäulen–Chirurgie: Instrumentarium Und Implantate Zur Wirbelsäulen–Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion,* Journal of Spinal Disorders, vol. 3, No. 1, pp. 77–86, ©1990 Raven Press, Ltd., New York.

Richard W. Porter, MD, FRCS, FRCSE, *Spinal Stenosis and Neurogenic Claudication,* SPINE vol. 21, No. 17, pp. 2046–2052, © 1996, Lippincott–Raven Publishers.

DEFLECTABLE SPACER FOR USE AS AN INTERSPINOUS PROCESS IMPLANT AND METHOD

PRIORITY CLAIM AND CROSS-REFERENCE TO RELATED APPLICATIONS

This is a continuation-in-part of U.S. patent application Ser. No. 10/037,236, filed on Nov. 9, 2001, which is a continuation-in-part of U.S. patent application Ser. No. 09/799,215, filed on Mar. 5, 2001, which is a continuation-in-part of U.S. patent application Ser. No. 09/179,570, filed on Oct. 27, 1998, now U.S. Pat. No. 6,048,342, which is a continuation-in-part of U.S. patent application Ser. No. 09/175,645, filed on Oct. 20, 1998, now U.S. Pat. No. 6,068,630. All of the above are incorporated herein by reference.

FIELD OF THE INVENTION

This invention relates to a spacer for use as an interspinous process implant. The implant placed between the spinous process of adjacent vertebrae in the spine is used to alleviate pain associated with the spine and surrounding tissues and structures.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example, with aging comes increases in spinal stenosis (including but not limited to central canal and lateral stenosis), the thickening of the bones which make up the spinal column, and facet antropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals and in particular for the elderly.

In addition, there are a variety of other ailments that can cause back pain in patients of all ages. For these ailments it is also desirable to eliminate such pain without major surgery.

Accordingly, there needs to be developed implants for alleviating such conditions which are minimally invasive, can be tolerated by patients of all ages and in particular the elderly, and can be performed preferably on an out patient basis.

SUMMARY OF THE INVENTION

The present invention is directed to providing a minimally invasive implant for alleviating discomfort associated with the spinal column. The implant includes a spacer which is self-aligning relative to the uneven surfaces of the spinous process. The spacer can further have an inner and outer spacer which can have the outer spacer movably mounted on the inner spacer. A variety of cross-sectional shapes are contemplated for the spacer including: elliptical, oval, ovoid, football-shaped, and rectangular or elongated with rounded ends.

The spacer is characterized in that it is comprised of a deflectable material. Suitable materials include, for example, polyetheretherketone (PEEK™) and polyetherketoneketone (PEKK). Other material that can be used include polyetherketone (PEK), polyetherketoneetherketoneketone (PEKEKK), and polyetherketoneketone (PEEKK), and generally a polyaryletheretherketone. Further other polyketones can be used as well as other thermoplastics. The spacer can also be made of titanium. Such materials are advantageously radio-translucent or transparent to x-rays. Additional suitable materials can be selected from the groups including by way of examble, include: high molecular weight polymers, and thermoplastics. Thus, the deflectable nature of the spacer enables the implant to further accommodate a specific patient's anatomy. Other aspects, objects, features and elements of embodiments of the invention are described or evident from the accompanying specification, claims and figures.

BRIEF DESCRIPTION OF THE DRAWINGS

FIGS. 1A–1F.

DETAILED DESCRIPTION OF THE PREFERRED EMBODIMENTS OF THE INVENTION

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference.

Figure 1A:
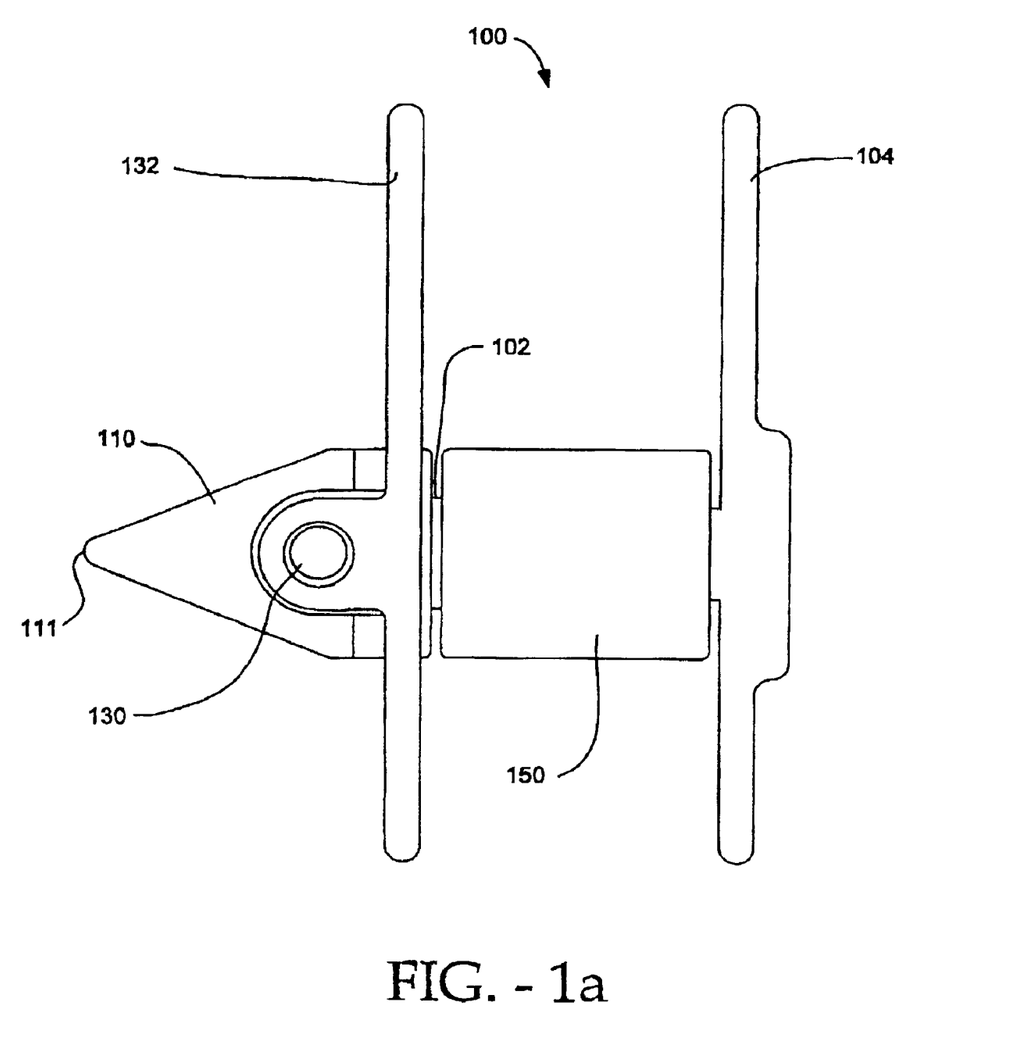
FIG. 1A is a front plan view of an embodiment of an assembled implant of the invention.
Figures 1B, 1C:
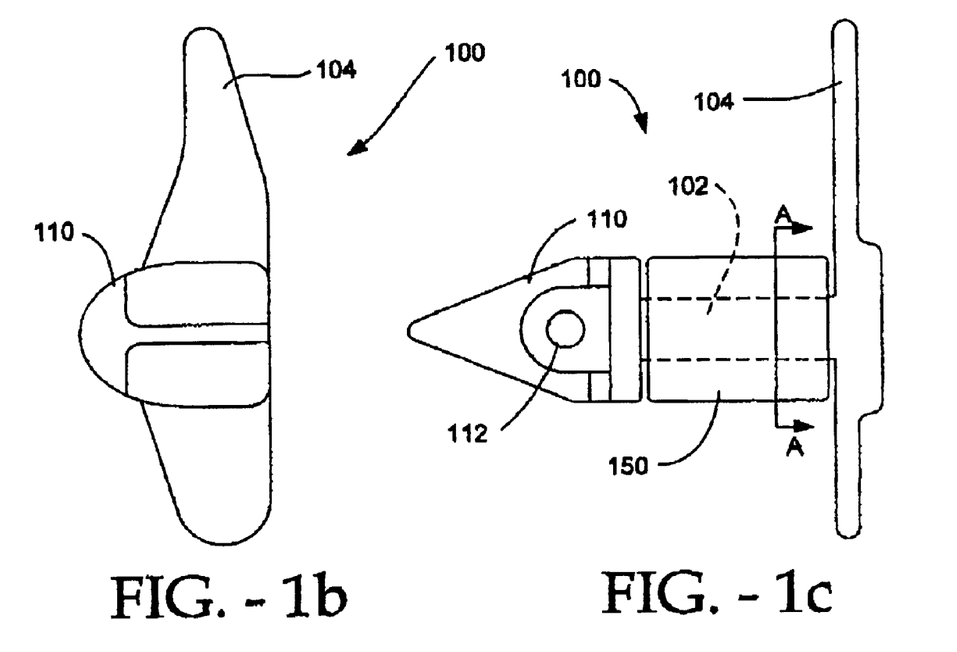
FIG. 1B is a left side view of the embodiment of the invention of FIG. 1A.
FIG. 1C is a front plan view of the embodiment of the invention of FIG. 1A including a spacer, a main body and a first wing.
Figure 1D:
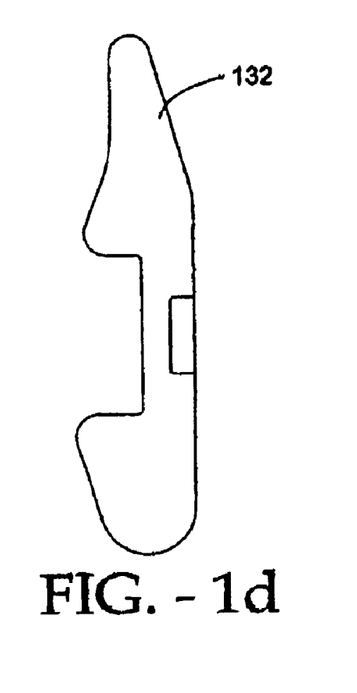
FIG. 1D is a left side view of the second wing of the embodiment of the invention of FIG. 1A.
Figure 1E:
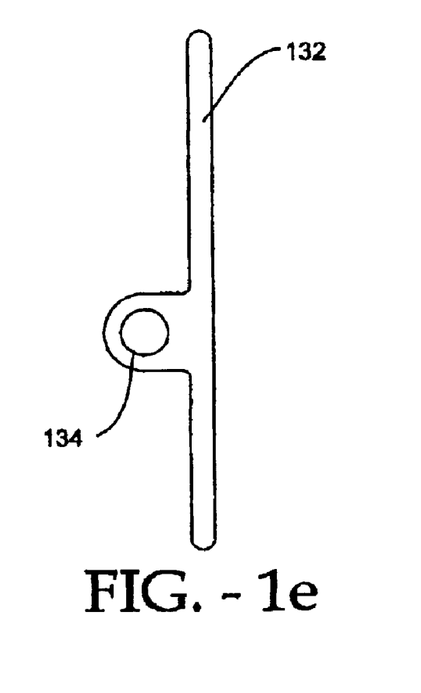
FIG. 1E is a front plan view of the second wing of the embodiment of the invention of FIG. 1A.

An embodiment of an implant 100 of the invention is depicted in FIG. 1A. This implant 100 includes a first wing 104 and a spacer 150 and a lead-in and distraction guide 110. This embodiment further can include, as required, a second wing 132. As can be seen in FIG. 1A, a shaft 102 extends from the first wing 104 and is the body that connects the first wing 104 to the distraction guide 110. Also, as can be seen in FIGS. 1A and 1B, the guide 110 in this particular embodiment is pointed in order to allow the implant to be inserted between adjacent spinous processes. In this particular embodiment, the guide 110 has an expanding cross-section from the distal end 111 to the area where the second wing 132 is secured to the guide 110. In this embodiment the guide 110 is wedge-shaped.

Figure 1F:
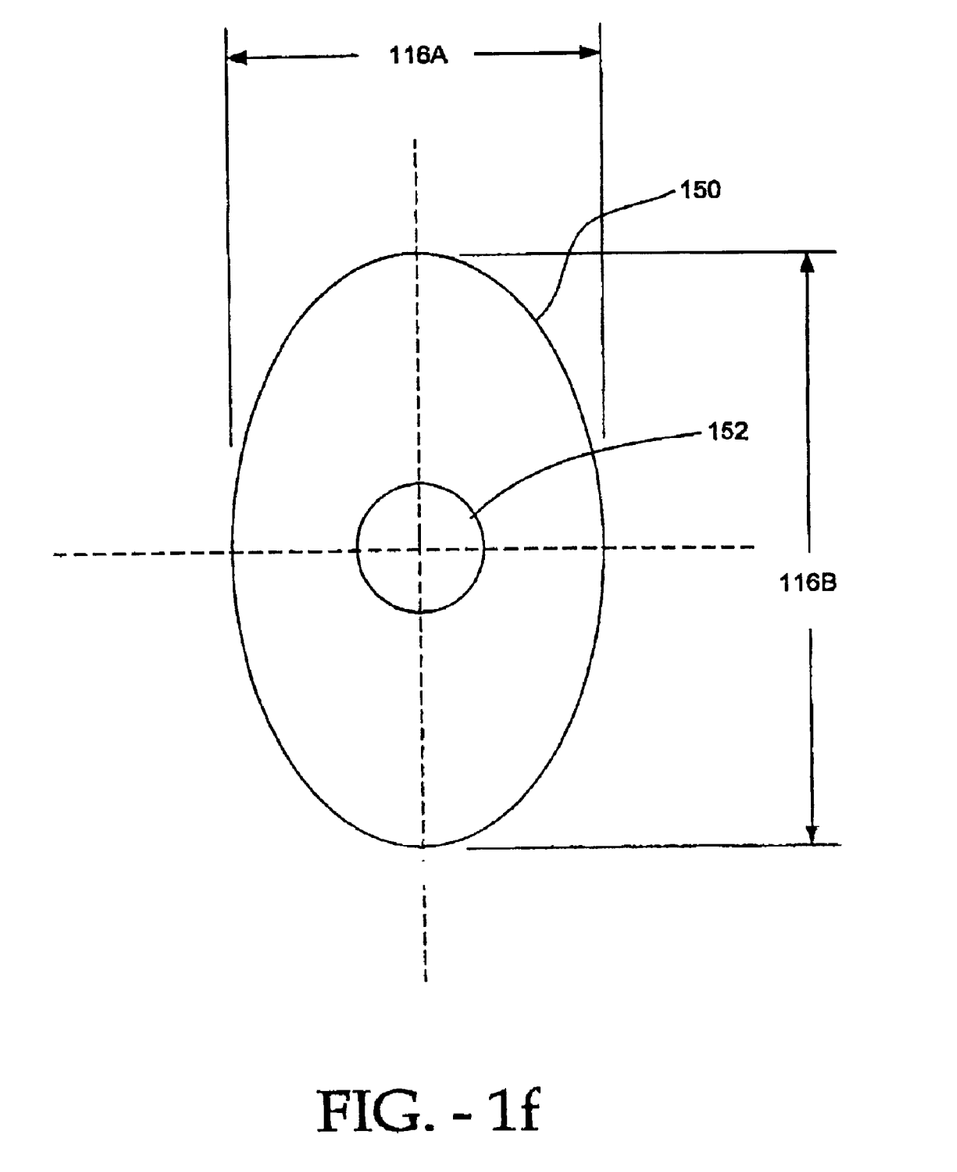
FIG. 1F is an end view of the spacer of the embodiment of the invention of FIG. 1A.

Additionally, as can be seen in FIGS. 1A, and 1F, the spacer 150 is elliptical shaped in cross-section. The spacer 150 can have other shapes such as circular, oval, ovoid, football-shaped, and rectangular-shaped with rounded corners and other shapes, and be within the spirit and scope of the invention. In this preferred embodiment, spacer 150 includes a bore 152 which extends the length of spacer 150. The spacer 150 is received over the shaft 102 of the implant 100 and can rotate thereon about the shaft 102. In these embodiments, the spacer 150 can have minor and major dimensions as follows:

| Minor Dimension (116a) | Major Dimension (116 b) |
|---|---|
| 6 mm | 13.7 mm |
| 8 mm | 14.2 mm |
| 10 mm | 15.2 mm |
| 12 mm | 16.3 mm |
| 14 mm | 17.8 mm |

The advantage of the use of the spacer 150 as depicted in the embodiment of FIG. 1A is that the spacer 150 can be rotated and repositioned with respect to the first wing 104, in the embodiment, in order to more optimally position the implant 100 between spinous processes. It is to be understood that the cortical bone or the outer bone of the spinous processes is stronger at an anterior position adjacent to the vertebral bodies of the vertebra than at a posterior position distally located from the vertebral bodies. Also, biomechanically for load bearing, it is advantageous for the spacer to be close to the vertebral bodies. In order to facilitate this and to accommodate the anatomical form of the bone structures, as the implant is inserted between the spinous processes and/or urged toward the vertebral bodies, the spacer 150 rotates relative to the wings, such as wing 104, so that the spacer 150 is optimally positioned between the spinous processes, and the wing 104 is optimally positioned relative to the spinous processes.

As required, implant 100 can also include a second wing 132 which fits over the guide 110 and is secured by a bolt 130 placed through apperture 134 of second wing 132 to the threaded bore 112 located in guide 110. As implanted, the first wing 104 is located adjacent to first sides of the spinous processes and the second wing 132 is located adjacent to second sides of the same spinous processes.

In another embodiment, the spacer 150 has a cross-section with a major dimension and a minor dimension, wherein the major dimension is greater than the minor dimension and, for example, less than about two times the minor dimension. It is to be understood that the spacer 150 can be fabricated from somewhat flexible and/or deflectable material.

In this embodiment the spacer is made out of a polymer, more specifically the polymer is a thermoplastic. Still more specifically the polymer is a polyketone known as polyetheretherketone (PEEK™). Still more specifically the material is PEEK 450G, which is an unfilled PEEK approved for medical implantation available from Victrex of Lancashire, Great Britain. (Victrex is located at www-.matweb.com or see Boedeker www.boedeker.com). Other sources of this material include Gharda located in Panoli, India (www.ghardapolymers.com). The spacer 150 can be formed by extrusion, injection, compression molding and/or machining techniques. This material has appropriate physical and mechanical properties and is suitable for carrying and spreading the physical load between the spinous process. For example in this embodiment the PEEK has the following approximate properties:

| | |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 Gpa |

It should be noted that the material selected may also be filled. For example, other grades of PEEK are also available and contemplated, such as 30% glass-filled or 30% carbon filled, provided such materials are cleared for use in implantable devices by the FDA, or other regulatory body. Glass filled PEEK reduces the expansion rate and increases the flexural modulus of PEEK relative to that which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

In this embodiment as described above the spacer 150 is manufactured from polyetheretherketone (PEEK™), available from Victrex. As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention. The spacer can also be comprised of polyetherketoneketone (PEKK).

Other material that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics. The spacer can also be made of titanium.

Reference to appropriate polymers that can be used in the spacer can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Figure 2A:
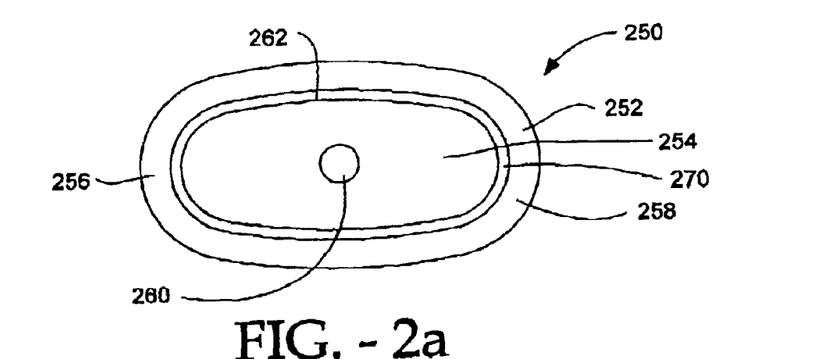
FIGS. 2A and 2B are an end and a perspective view of still another embodiment of the spacer of the invention.

Referring now to FIGS. 2A–5B, various embodiments of spacers are depicted. Turning now to FIGS. 2A, 2B, 2C the spacer 250 includes an outer spacer 252 and an inner spacer 254. Inner spacer 254 has a bore 260 therethrough that enables the spacer 250 to rotate about the shaft 102 of implant 100 shown in FIG. 1A.

Figure 2B:
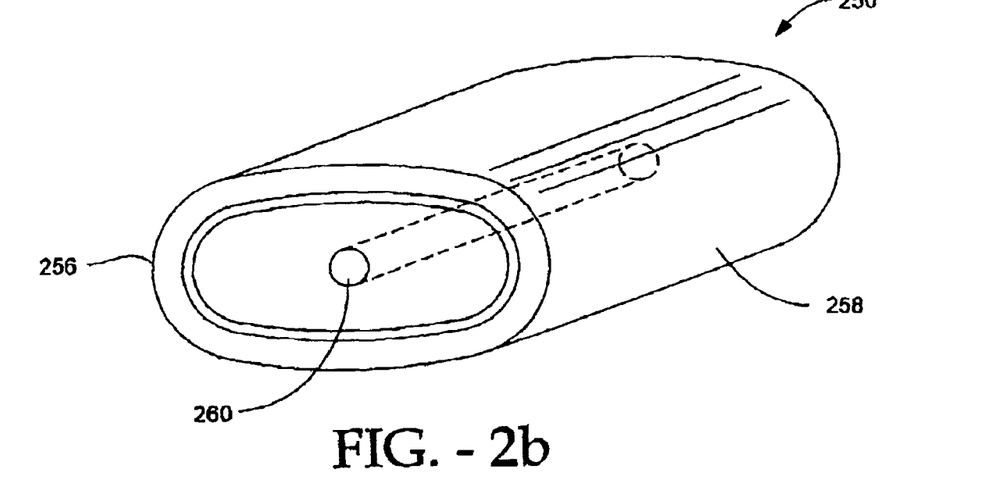
Figure 2C:
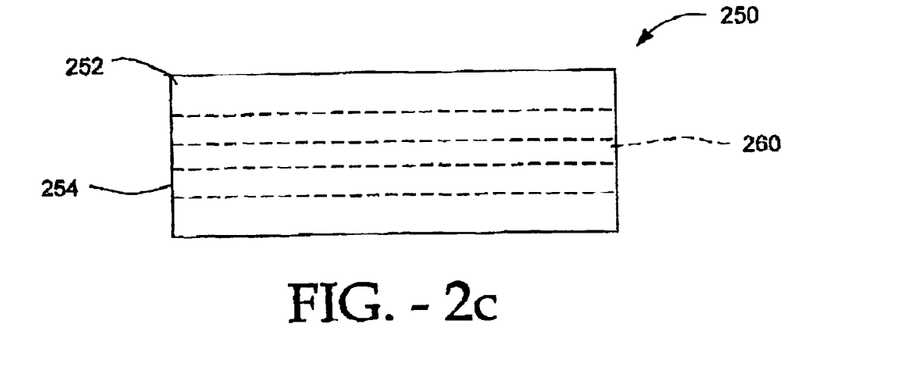
FIG. 2C is a front view of the spacer of FIG. 2A.

Each of the inner and outer spacers of the spacer 250 can have a cross-section that is elliptical, oval, ovoid, football-shaped, circular-shaped, rectangular with rounded ends (where the cross-section has two somewhat flattened surfaces and two rounded surfaces similar to the effect of a flattened ellipse). Further, the inner spacer and outer spacer can have different cross-sectional shapes relative to each other. At least the minor outer diameter of the outer spacer is between 6 mm and 14 mm. Typically the minor outer dimension is one of 6 mm, 8 mm, 10 mm, 12 mm, and 14 mm. The different sizes enable the spacer to accommodate different sized patients.

As depicted in FIG. 2A the spacer 250 is a rectangle with rounded ends or a flattened ellipse, as it has two sides that are almost parallel to each other, and the ends connecting the parallel sides are curved, similar to a "race-track." Thus, in this and other embodiments the two sides or surfaces of the spacer, including the upper and the lower spacer can also be flattened or slightly radiused. The bore 260 is located in the center of the inner spacer 254 and there is a gap 262 between the upper and lower portions of the outer spacer 252 and the inner spacer 254. A gap 270 is provided between the inner and outer spacers at the rounded ends 256, 258. In a preferred embodiment for about an 8 millimeter spacer 250, the upper and lower gaps 262 are about 0.012 of an inch or about a quarter of a millimeter each for a total combined gap of about one half of a millimeter. The gaps 270 at the curved ends 256, 258 are about 0.002 of an inch or slightly less than a tenth of a millimeter each in a preferred embodiment. The gap 270 for all of the other spacers is preferably as specified above for the 8 mm spacer. For the 6 millimeter spacer, generally this is made of one piece such as seen in FIG. 1F. However for the other spacers, these spacers are preferably made of two pieces as seen for example in FIG. 2A. The table below sets our preferred dimensions for the combined upper and lower gap dimension for the spacers.

| Spacer Minor Dimension | Total Combined Gap Dimension |
| --- | --- |
| 6 mm | n/a |
| 8 mm | .020 in (0.51 mm) |
| 10 mm | 0.025 in (0.64 mm) |
| 12 mm | 0.030 in (0.76 mm) |
| 14 mm | 0.035 in (0.89 mm) |

The gap 262 close and the inner and outer spaces touch each other when the spacer is loaded with 800 newtons of force. The design is made to take repeated loading at 1200 newtons of force.

In the above embodiment the outer spacer 252 is movably or slidably mounted on the inner spacer 254, and the inner spacer 254 is rotatably mounted on the shaft 102 of the implant 100.

As discussed above, the spacer, including either the inner spacer or outer spacer, or both, can be made of deflectable and flexible material. As discussed above, suitable material is a polymer such as for example polyetheretherketone (PEEK™). Other suitable materials can include those described above. Further titanium can be used.

Further, the deflectable or flexible material can have a graduated stiffness to help gradually distribute the load when the spinous processes place a force upon the exterior surface of the outer spacer. This can be accomplished by forming multiple layers of the deflectable or flexible material with decreasing stiffness or hardness from the center of the spacer outwardly. Alternatively, the material can have a higher stiffness or hardness in the center of the inner spacer.

Persons of skill in the art will appreciate that the embodiments shown in FIGS. 3A–5B can be made of the materials similar to those emphasized in the embodiment shown in FIGS. 1A and 2A.

Figure 3A:
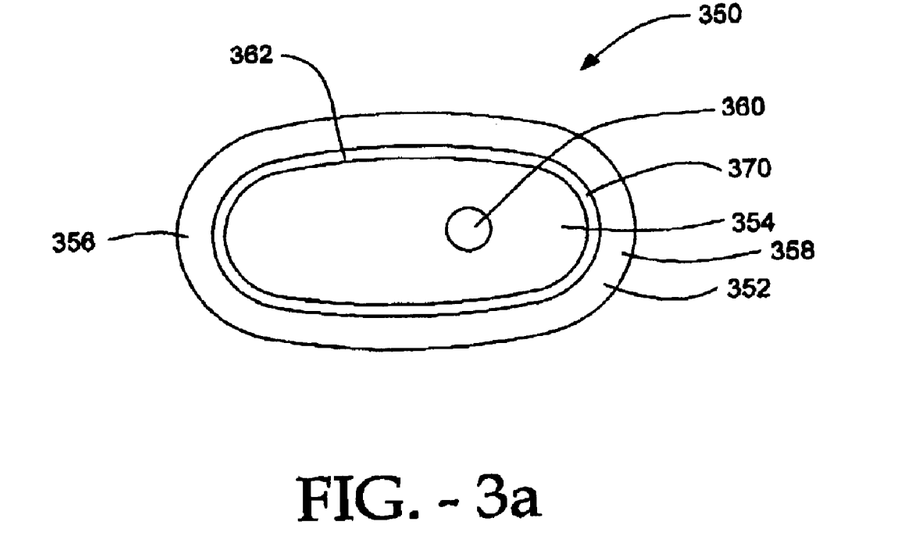
FIGS. 3A and 3B are an end and a perspective view of yet another embodiment of the spacer of the invention.
Figure 3B:
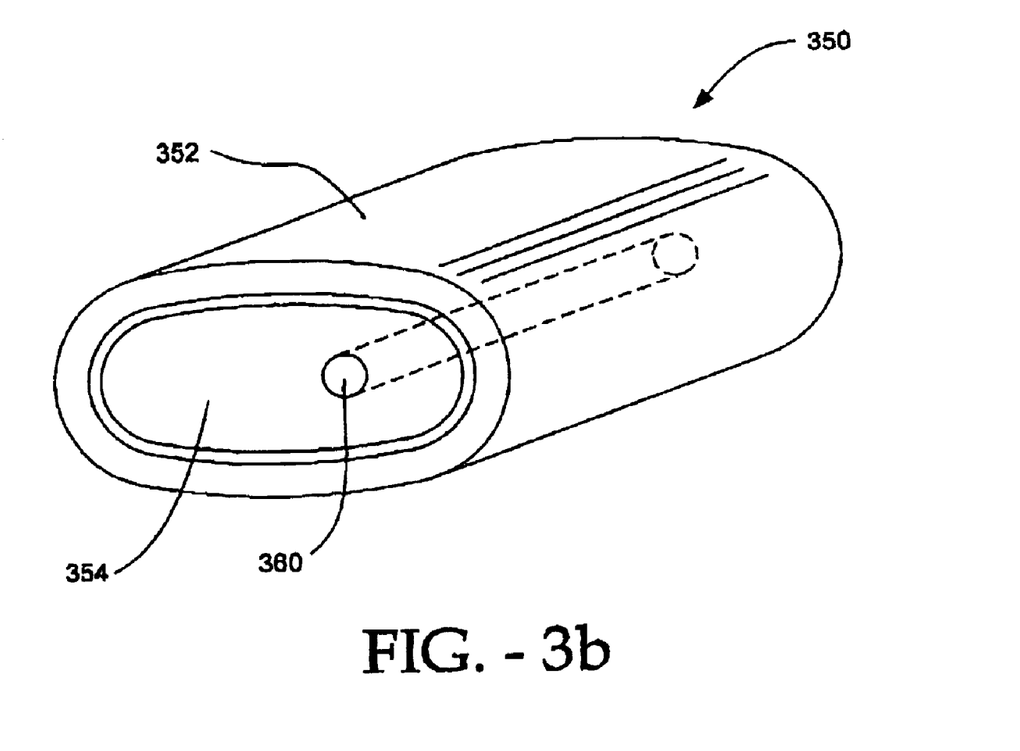

Now referring to FIGS. 3A, 3B again the spacer 350 is depicted as a somewhat flattened ellipse with rounded ends 356, 358, where two sides are somewhat parallel to each other and the ends connecting the parallel sides are curved, similar to a "race-track." The bore 360 is located off-center within the inner spacer 354. Further, there are gaps 362, 370 between the outer spacer 352 and the inner spacer 354. Except for the location of the bore 360, the dimensions and materials of the embodiment of FIGS. 3a, 3b are similar to that of FIGS. 2a, 2b.

The off-center bore 360 allows a greater portion of the spacer 350 to be positioned close to the vertebral bodies. With an ovoid ("egg-shaped") spacer, off-set the bore 360 is preferably close to the bulbous end of the spacer with the more pointed end directed toward the vertebral bodies in order to attain the advantages of the spacer being closer to the vertebral bodies and enhanced distributed load bearing.

Figures 4A, 4B:
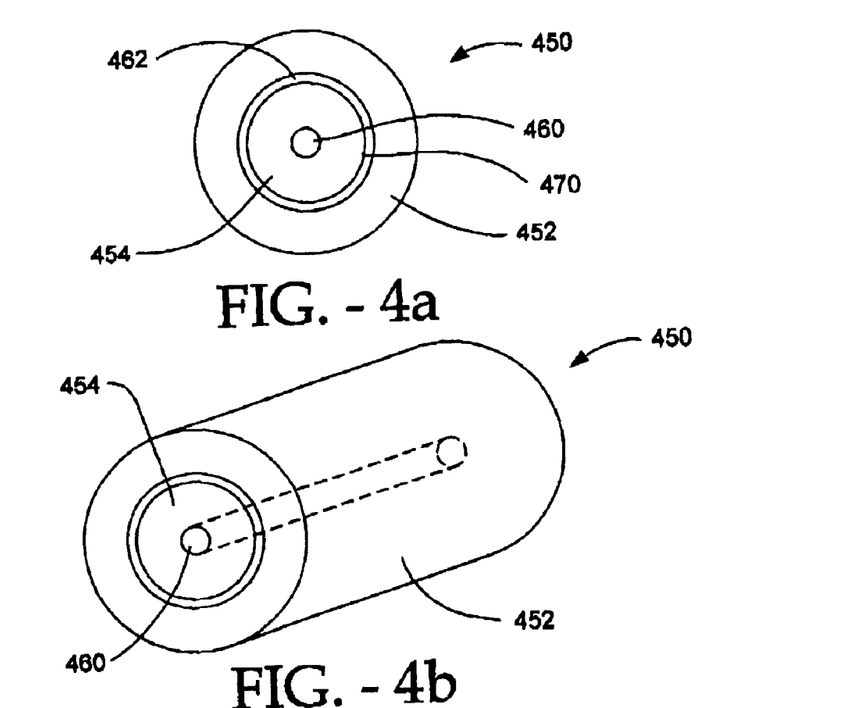
FIGS. 4A and 4B are an end and a perspective view of still another embodiment of the spacer of the invention.

Turning now to FIG. 4, the spacer 450 is depicted as having a circular cross-section. The bore 460 is located within the inner spacer 454. Further, there are gaps 462, 470 between the outer spacer 452 and the inner spacer 454. The dimensions of the gap would be the same as those discussed with respect to the embodiment shown in FIG. 2a. The embodiment of FIG. 4a can have a diameter that is the minor diameter of the embodiments shown in FIGS. 1A, 2A, and 3A.

Also, as will be appreciated by those in skill in the art, the outer spacer 452 can be movably mounted on the inner spacer 454 and the inner spacer 454 can be rotatably mounted on the shaft 102 of the implant 100 or any other suitable implant.

Figure 5A:
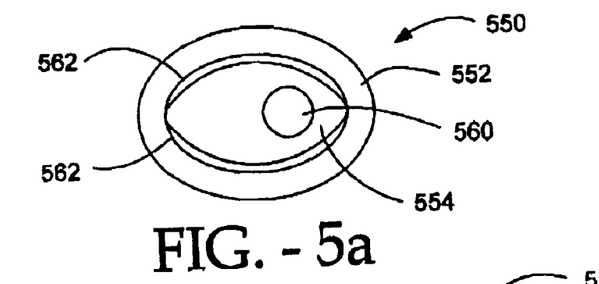
FIGS. 5A and 5B are an end and a perspective view of yet another embodiment of the spacer of the invention.
Figure 5B:
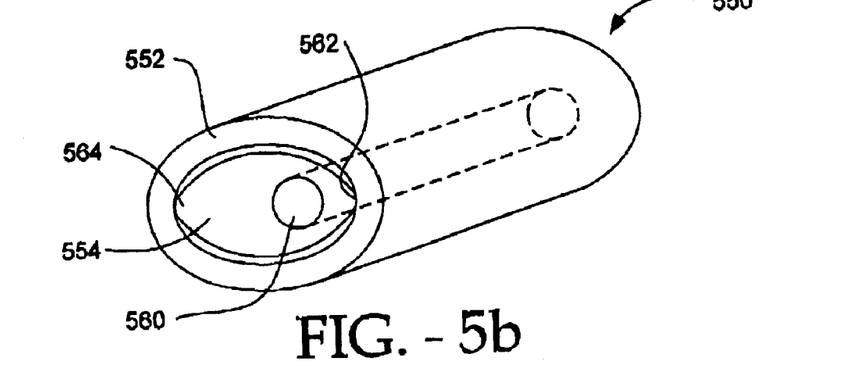

In FIG. 5A, 5B, the spacer 550 is depicted as having an outer spacer 552 and an inner spacer 554 of two different cross-sectional shapes. In this embodiment, the outer spacer 552 is elliptical and the inner spacer is football shaped in cross-sections. The bore 560 is located off-center within the inner spacer 554. However, as will be appreciated by those of skill in the art, the bore 560 can be located centrally within the inner spacer without departing from the scope of the invention.

The gaps 562 between the outer spacer 552 and the inner spacer 554 are crescent-shaped as a result of the inner and outer spacers have different cross-sectional shapes. Thus the gap can have a width ranging from approximately between 0.25 mm at the minor diameter (greatest vertical height) to just enough space at the apexes 562, 564 of the inner spacer 554 so that the outer spacer can slide over the inner spacer. The inner spacer 554 can be rotatably mounted on the shaft 102 of the implant 100.

The embodiment of this implant as well as the several other implants described herein act to limit extension (backward bending) of the spine. These implants, however, do not inhibit the flexion (forward bending) of the spinal column.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and their equivalence.

What is claimed:

1. An implant adapted to be placed between spinous processes comprising:
   a body having a shaft extending therefrom;
   a spacer that is rotatably mounted on the shaft;
   wherein said spacer is comprised of a deflectable material; and
   wherein said spacer is comprised of:
      an inner spacer that is rotatably mounted about the shaft and
      an outer spacer that is mounted on said inner spacer.

2. The implant of claim 1 wherein:
   said inner spacer has one of a flattened or a slightly radiused upper and lower surfaces and rounded first and second end, and
   said outer spacer has one of a flattened or a slightly radiused upper and lower surfaces and rounded first and second ends.

3. The implant of claim 1 wherein:
   said inner spacer and said outer spacer have a cross-section shape selected from the group consisting of elliptical-shaped, cylindrical-shaped, ovoid-shaped, oval-shaped, track-shaped, football-shaped and rectangle-shaped with curved ends.

4. The implant of claim 1 wherein the inner spacer and the outer spacer is selected from the group consisting of polyetheretherketone and polyetherketoneketone.

5. The implant of claim 1 wherein:
   said inner spacer has upper and lower outer surfaces; and
   said outer spacer has upper and lower inner surfaces; and
   wherein said inner surface of said outer spacer are spaced from the outer surface of said inner spacers.

6. The implant of claim 1 wherein at least one of said inner spacer and said outer spacer is comprised of a polycarbonate urethane.

7. An implant adapted to be placed between spinous processes comprising:
   a body having a shaft extending therefrom;
   a spacer that is rotatably mounted on the shaft;
   wherein said spacer is comprised of a deflectable material; and
   wherein said spacer is comprised of
      an inner spacer that is rotatably mounted about the shaft; and
      an outer spacer that is movably mounted relative to said inner spacer.

8. The implant of claim 7 wherein said outer spacer is slidably mounted on said inner spacer.

9. An implant adapted to be placed between spinous processes comprising:
   a body having a shaft extending therefrom;
   a spacer that is rotatably mounted on the shaft;
   wherein said spacer is comprised of a deflectable material; and
   wherein said spacer is comprised of:
      an inner spacer that is rotatably mounted about the shaft; and
      an outer spacer that is mounted on said inner spacer; and
      at least one of said inner spacer and said outer spacer is comprised of one of the group consisting of polyetheretherketone and polyetherketoneketone.

10. An implant adapted to be placed between spinous processes comprising:
    a body having a shaft extending therefrom;
    a spacer that is rotatably mounted on the shaft; and
    wherein said spacer is comprised of;
       an inner spacer that is rotatably mounted about the shaft; and
       an outer spacer that is mounted on said inner spacer.

11. The implant of claim 10 wherein said outer spacer is movably mounted on said inner spacer.

12. The implant of claim 10 wherein:
    at least one of said inner spacer and said outer spacer is selected from the group consisting of polyetheretherketone and polyetherketoneketone.

13. The implant of claim 10 wherein said spacer is one of elliptical-shaped, cylindrical-shaped, ovoid-shaped, oval shaped, track-shaped and rectangular-shaped with curved ends.

14. The implant of claim 10 wherein said spacer is selected from the group consisting of: polyetheretherketone, polyetherketoneketone, a polyaryletheretherketone, a high molecular weight polymer, a thermoplastic, and a polycarbonate urethane.

15. The implant of claim 10 wherein said inner spacer and said outer spacer is selected from the group consisting of polyetheretherketone and polyetherketoneketone.

16. The implant of claim 10 wherein:
    said inner spacer has flattened upper and lower portions and rounded first and second end, and
    said outer spacer has flattened upper and lower portions and rounded first and second ends.

17. The implant of claim 10 wherein:
    said inner spacer has upper and lower outer portions; and
    said outer spacer has upper and lower inner portions; and
    wherein said upper portions of said outer spacer are spaced from the upper portion of said inner spacer; and
    wherein said lower portions of said outer spacer is spaced from the lower portion of said inner spacer.

18. The implant of claim 10 wherein said spacer is comprised of a material that is deflectable.

19. The implant of claim 10 wherein said spacer is comprised of a material that is sufficiently deflectable so that said outer spacer can be urged into contact with the inner spacer with the implant placed between spinous processes of a human and with the human bending backwards.

20. The implant of claim 19 wherein the spacer is radio-translucent.

21. The implant of claim 10 wherein:
    said inner spacer has flattened upper and lower portions; and
    said outer spacer has flattened upper and lower portions; and
    wherein said upper portion of said outer spacer is spaced from the upper portion of said inner spacer; and
    wherein said spacer is comprised of a material that is sufficiently deflectable so that said flattened upper and lower portion of said outer spacer can be urged into contact with the respective flattened upper and lower portions of said inner spacer with the implant placed between spinous processes of a human and with the human bending backwards.

22. The implant of claim 10 wherein:
    said spacer has dimensions of selected from the group consisting of 6 mm, 8 mm, 10 mm, 12 mm, and 14 mm.

23. The implant of claim 10 wherein:
said outer spacer can have an outer dimension selected from the group consisting of 6 mm, 8 mm, 10 mm, 12 mm, and 14 mm; and
said inner spacer has flattened upper and lower portions; and
said outer spacer has flattened upper and lower portions; and
wherein said outer spacer is spaced from the upper portion of said inner spacer by about at least one quarter millimeter; and
wherein said outer spacer is spaced from the lower portion of said inner spacer by about at least one quarter millimeter.

24. The implant of claim 10 wherein said spacer has rounded ends, and upper and lower surfaces.

25. The implant of claim 10 wherein:
said inner spacer has upper and lower surfaces and rounded first and second end, and
said outer spacer has upper and lower surfaces and rounded first and second send.

26. The implant of claim 10 wherein:
said inner spacer has an off-center bore that receives said shaft so that said spacer can rotate about said shaft.

27. The implant of claim 10 wherein:
said inner spacer is football-shaped in cross-section; and
said outer spacer has a cross-section selected from the group consisting of elliptical-shaped, cylindrical-shaped, ovoid-shaped, oval-shaped, track-shaped, and rectangle-shaped with curved ends.

28. The implant of claim 10 wherein:
said inner spacer has upper and lower surfaces and substantially pointed first and second end; and
said outer spacer has upper and lower surfaces and substantially rounded first and second ends.

29. The implant of claim 10 wherein:
said inner spacer has upper and lower portions and first and second end, and
said outer spacer has upper and lower portions and firs and second ends; and
said respective ends are placed closer together than said respective portions.

30. The implant of claim 10 wherein the spacer has a dimension selected from about 6 mm to about 14 mm.

31. The implant of claim 10 wherein at least one of said inner space and said outer spacer is comprised of a polymer.

32. The implant of claim 10 wherein at least one of said inner spacer and said outer spacer is comprised of thermoplastic.

33. The implant of claim 10 wherein at least one of said inner spacer and said outer spacer is comprised of polyketone.

34. The implant of claim 10 wherein at least one of said inner spacer and said outer spacer is selected from the group consisting of polyetheretherketone, and polyetherketoneketone.

35. The implant of claim 10 wherein at least one of said inner spacer and said outer spacer is comprised of a polycarbonate urethane.

36. The implant of claim 10 wherein at least one of said inner spacer and said outer spacer is comprised of a urethane.

37. The implant of claim 10 wherein the spacer is radiotranslucent.

38. The implant of claim 10 wherein the spacer is transparent to x-rays.

39. The implant of claim 10 wherein at least one of the inner spacer and the outer spacer is selected from polyetherketone, polyetherketoneetherketoneketone, polyaryleetheretherketone, and polyetheretherketoneketone, and titanium.

40. The spacer of claim 10 wherein:
said spacer has an off-center bore that receives said shaft so that said spacer can rotate about said shaft.

41. A spacer for use with an interspinous implant comprising:
an inner spacer adapted to be rotatably mounted on a shaft of the implant; and
an outer spacer mounted on the inner spacer;
wherein the outer spacer is movable mounted over the inner spacer.

42. An implant adapted to be placed between spinous processes comprising;
a body having a shaft extending therefrom;
a spacer that is mounted on the shaft; and
wherein said spacer is comprised of:
an inner spacer that is mounted on said shaft; and
an outer spacer that is mounted on said inner spacer;
wherein at least one of said inner spacer and said outer spacer is selected from the group consisting of polyetheretherketone and polyetherketoneketone.

43. In an implant that is locatable between spinous processes, the improvement comprising:
a spacer with an inner spacer that is rotabably mounted on a shaft of the implant; and
said spacer having an outer spacer mounted on the inner spacer;
wherein:
said inner spacer has flattened upper and lower portions and rounded first and second end, and
said outer spacer has flattened upper and lower portions and rounded first and second ends.

44. In an implant that is locatable between spinous processes, the improvement comprising:
a spacer with an inner spacer that is rotabably mounted on a shaft of the implant; and
said spacer having an outer spacer mounted on the inner spacer;
wherein:
said inner spacer has flattened upper and lower portions; and
said outer spacer has flattened upper and lower portions; and
wherein said upper portion of said outer spacer is spaced from the upper portion of said inner spacer; and
wherein said lower portion of said outer spacer is spaced from the lower portion of said inner spacer; and
wherein said spacer is comprised of a material that is sufficiently deflectable so that said flattened upper and lower portion of said outer spacer can be urged into contact with the respective flattened upper and lower portions of said inner spacer within the implant placed between spinous processes of a human and with the human bending backwards.

45. In an implant that is locatable between spinous processes, the improvement comprising:
a spacer with an inner spacer that is rotabably mounted on a shaft of the implant; and said spacer having an outer spacer mounted on the inner spacer;

wherein at least one of said inner spacer and said outer spacer is selected from the group consisting of polyetheretherketone and polyetherketoneketone.

46. In an implant that is locatable between spinous processes, the improvement comprising:

a spacer with an inner spacer that is rotabably mounted on a shaft of the implant; and said spacer having an outer spacer mounted on the inner spacer;

wherein:

said inner spacer has upper and lower outer portions; and said outer spacer has upper and lower inner portions; and wherein said upper portion of said outer spacer are spaced from the lower portion of said inner spacer.

47. A spacer for use with an interspinous implant comprising:

an inner spacer adapted to be rotatably mounted on a shaft of the implant; and an outer spacer mounted on the inner spacer;

wherein the spacer is translucent to x-rays.

48. An implant adapted to be placed between spinous processes comprising:

a body having a shaft extending therefrom;

a spacer that is mounted on the shaft; and wherein said spacer is comprised of:

an inner spacer that is mounted on said shaft; and an outer spacer that is mounted on said inner spacer;

wherein the spacer is radio-translucent.

49. An implant adapted to be placed between spinous processes comprising:

a body having a shaft extending therefrom;

a spacer that is mounted on the shaft; and wherein said spacer is comprised of:

an inner spacer that is mounted on said shaft; and an outer spacer that is mounted on said inner spacer;

wherein the spacer is transparent to x-rays.

* * * * *